(12) United States Patent
Hughes

(10) Patent No.: US 8,448,676 B2
(45) Date of Patent: May 28, 2013

(54) MULTIPLE SUMP FUEL SAMPLER WITH CATCH CAN

(75) Inventor: William C. Hughes, Woodstock, IL (US)

(73) Assignee: Innoquest, Inc., Woodstock, IL (US)

( * ) Notice: Subject to any disclaimer, the term of this patent is extended or adjusted under 35 U.S.C. 154(b) by 703 days.

(21) Appl. No.: 12/688,969

(22) Filed: Jan. 18, 2010

(65) Prior Publication Data

US 2010/0186850 A1      Jul. 29, 2010

Related U.S. Application Data

(60) Provisional application No. 61/206,084, filed on Jan. 27, 2009.

(51) Int. Cl.
| | | |
|---|---|---|
| *B65B 1/04* | (2006.01) | |
| *G01N 1/00* | (2006.01) | |
| *B67D 7/32* | (2010.01) | |
| *G01N 1/20* | (2006.01) | |

(52) U.S. Cl.
   CPC ............ B67D 7/3209 (2013.01); G01N 1/2035 (2013.01)
   USPC ............. 141/86; 141/112; 141/301; 141/352; 73/863.86

(58) Field of Classification Search
   USPC .................. 141/112, 301, 319, 352, 363–366, 141/86; 436/181; 73/863.86
   See application file for complete search history.

(56) References Cited

U.S. PATENT DOCUMENTS

| 2,844,964 | A | * | 7/1958 | Guibert ...................... 73/863.86 |
|---|---|---|---|---|
| 3,011,349 | A | | 12/1961 | Kratz |
| 3,198,016 | A | * | 8/1965 | Poorman .................... 73/863.86 |
| 3,976,572 | A | | 8/1976 | Reick |
| 4,004,463 | A | * | 1/1977 | Puthoff et al. ............. 73/864.66 |
| 4,289,027 | A | | 9/1981 | Gleaves et al. |
| 4,689,306 | A | * | 8/1987 | Redikultsev et al. ....... 435/309.2 |
| 4,700,580 | A | | 10/1987 | Kamin |
| 4,967,595 | A | | 11/1990 | Olson |
| 4,991,635 | A | * | 2/1991 | Ulm ............................. 141/346 |
| 5,359,905 | A | | 11/1994 | Brodbeck |
| 5,620,434 | A | * | 4/1997 | Brony ........................... 604/406 |
| 6,715,624 | B2 | * | 4/2004 | Brockwell .................... 215/247 |
| 6,991,724 | B2 | | 1/2006 | Brodbeck et al. |
| 7,374,054 | B2 | * | 5/2008 | Brockwell .................... 215/311 |
| 7,377,151 | B1 | | 5/2008 | Magee |
| 7,491,328 | B2 | * | 2/2009 | Brodbeck et al. ............. 210/232 |
| 7,748,282 | B1 | | 7/2010 | Hohmann |
| 2008/0178664 | A1 | | 7/2008 | Brodbeck et al. |

* cited by examiner

*Primary Examiner* — Timothy L Maust
(74) *Attorney, Agent, or Firm* — Reinhart Boerner Van Deuren P.C.

(57) ABSTRACT

A multiple sump fuel sampler with catch can that includes an upper fuel sampling and testing reservoir with integral lower catch can reservoir arranged such that a self-closing valve is placed between the upper sampling reservoir and the lower catch can. This self-closing valve can be easily opened and closed by a user to allow fuel in the upper sampling reservoir to drain down into the lower catch can reservoir. Embodiments of the invention include a means of spill-free dumping of fuel accumulated in the lower catch can reservoir via an integral no-drip pour spout.

21 Claims, 4 Drawing Sheets

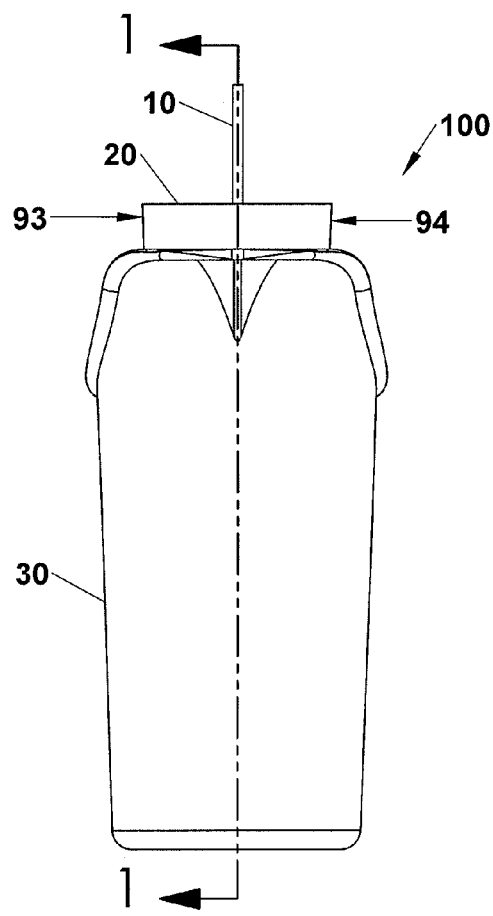
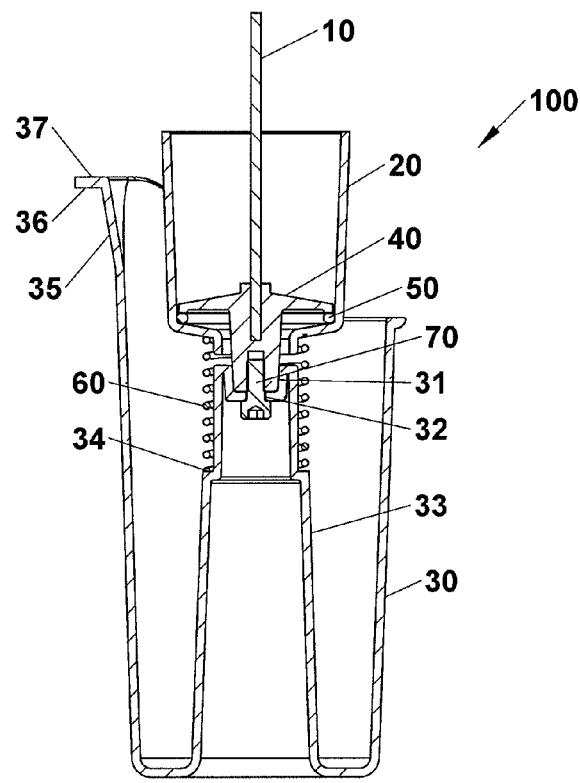
Fig. 3
Section 1-1
Fig. 4

Section 2-2

MULTIPLE SUMP FUEL SAMPLER WITH CATCH CAN

CROSS-REFERENCE TO RELATED PATENT APPLICATIONS

This patent application claims the benefit of U.S. Provisional Patent Application No. 61/206,084 filed Jan. 27, 2009, the entire teachings and disclosure of which are incorporated herein by reference thereto.

FIELD OF THE INVENTION

The present invention relates generally to fuel sampling containers, and, more particularly, to fuel sampling containers typically used in aviation.

BACKGROUND OF THE INVENTION

Among aircraft operators, sampling fuel before every flight is a common practice designed to promote aviation safety. However, some aircraft, especially more modern aircraft, may have multiple (e.g., as many as 13) fuel sumps located at various spots on the aircraft. With conventional fuel sampling containers, checking multiple fuel sumps can become very time-consuming.

It would therefore be desirable to have a fuel sampling container that speeds up the process of sampling fuel from multiple fuel sumps. Embodiments of the invention provide such a fuel sampling container. These and other advantages of the invention, as well as additional inventive features, will be apparent from the description of the invention provided herein.

BRIEF SUMMARY OF THE INVENTION

In one aspect, embodiments of the invention provide a multiple sump fuel sampler with catch can that includes an upper reservoir configured to hold a liquid, a lower reservoir coupled to the upper reservoir, the lower reservoir being larger than the upper reservoir, and a self-closing valve attached at the juncture of the upper and lower reservoirs. In an embodiment of the invention, the self-closing valve is configured to, when open, allow liquid in the upper reservoir to drain into the lower reservoir. An embodiment further includes a rod extending through at least a portion of the self-closing valve, through the interior of the upper reservoir and beyond an opening at the top of the upper reservoir, wherein the rod is configured to activate a fuel sump valve.

In another aspect, embodiments of the present invention provide a fuel sampling tester with integral lower catch can arranged such that a self-closing valve is placed between the upper sampling reservoir and the lower catch can reservoir. This self-closing valve is configured to be easily opened and closed by the user to allow fuel in the upper sampling reservoir to drain down into the lower catch can reservoir.

Other aspects, objectives and advantages of the invention will become more apparent from the following detailed description when taken in conjunction with the accompanying drawings.

BRIEF DESCRIPTION OF THE DRAWINGS

The accompanying drawings incorporated in and forming a part of the specification illustrate several aspects of the present invention and, together with the description, serve to explain the principles of the invention. In the drawings:

FIG. 3 is a front view of the multiple sump fuel sampler with catch can of FIG. 1;

FIG. 4 is a cross-sectional view of the multiple sump fuel sampler with catch can of FIG. 1 with a self-closing valve in the closed position;

While the invention will be described in connection with certain preferred embodiments, there is no intent to limit it to those embodiments. On the contrary, the intent is to cover all alternatives, modifications and equivalents as included within the spirit and scope of the invention as defined by the appended claims.

DETAILED DESCRIPTION OF THE INVENTION

In one aspect, embodiments of the present invention provide a multiple sump fuel sampler with catch can for sampling and visually inspecting aviation fuel from multiple fuel sumps on aircraft. One feature of the present invention is that it allows for each individual sample to be transferred to an integral lower catch can which holds multiple samples until all the sumps on the airplane have been checked. Once all the sumps have been checked, the fuel in the lower catch can be dumped into an appropriate fuel depository, or back into the airplane if the samples are clean. Embodiments of the invention allow for fuel from each sump to be individually inspected in the upper sampling reservoir before mixing with the larger fuel volume in the lower catch can. Embodiment of the invention combine the advantages of easy inspection of fuel from each sump with the advantage of a large volume to allow checking multiple sumps without having to empty each sample into a separate container. Further, embodiments of the present invention incorporate special pour spout features that eliminate spilling or dribbling when the lower catch can is emptied. In addition to sampling aviation fuel, embodiments of the invention have applications wherever fluids must be sampled and visually checked. One of ordinary skill in the art will recognize that this includes potential application on equipment and industries outside that of aircraft operation or maintenance.

Figure 1:
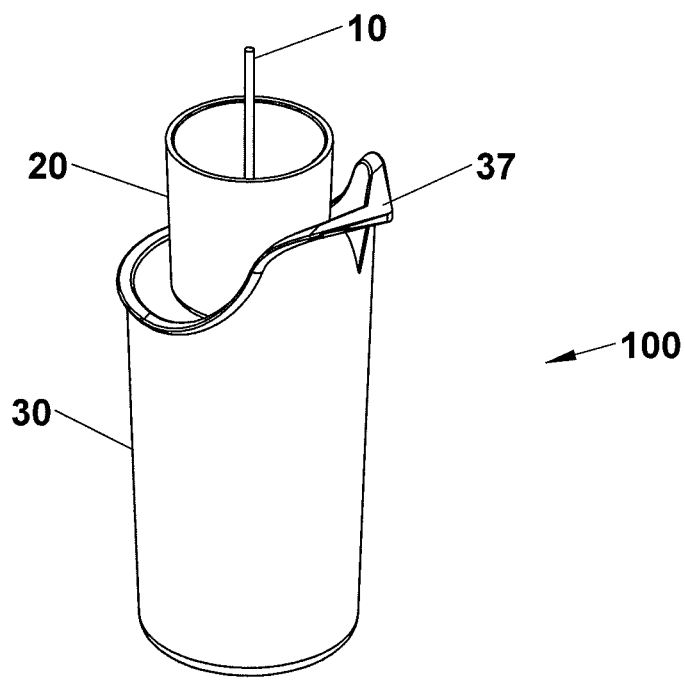
FIG. 1 is a perspective view of a multiple sump fuel sampler with catch can, according to an embodiment of the invention.

According to an embodiment of the invention, a multiple sump fuel sampler with catch can 100 is shown in FIGS. 1-7 and includes an upper sampling reservoir 20, which in at least one embodiment is made clear plastic, and a lower catch can reservoir 30 that can also be made from clear plastic, opaque plastic, or metal. The multiple sump fuel sampler with catch can 100 is typically held in a primarily upright position as shown in FIG. 1 to perform properly as described below due to the necessity of gravity to hold fuel in the reservoirs 20, 30, which have open tops.

In an embodiment of the invention, the volume of the lower reservoir 30 is several times the volume of the upper reservoir 20, allowing the lower reservoir 30 to hold many partial or full samples from the upper reservoir 20. Connection of the upper reservoir 20 to the lower reservoir 30 incorporates a self-closing valve comprised of end cap 40, O-ring 50, upper reservoir 20, and spring 60. A screw 70 attaches the end cap 40 to the lower reservoir 30 and hence holds the entire self-closing valve, as described above, together. In at least one embodiment, the multiple sump fuel sampler with catch can 100 has upper reservoir 20, end cap 40, and lower reservoir 30 made of clear plastic to allow for easy visual inspection of fuel samples for water or other contamination.

The design of the self-closing valve allows for finger pressure from any side to activate the valve and therefore allows users with different sized hands, or left or right hand preferences to activate the valve with equal ease. As used herein, a user is defined as one who would normally be expected to sample fuel from an aircraft, for example a licensed pilot or aircraft mechanic.

Figure 7:
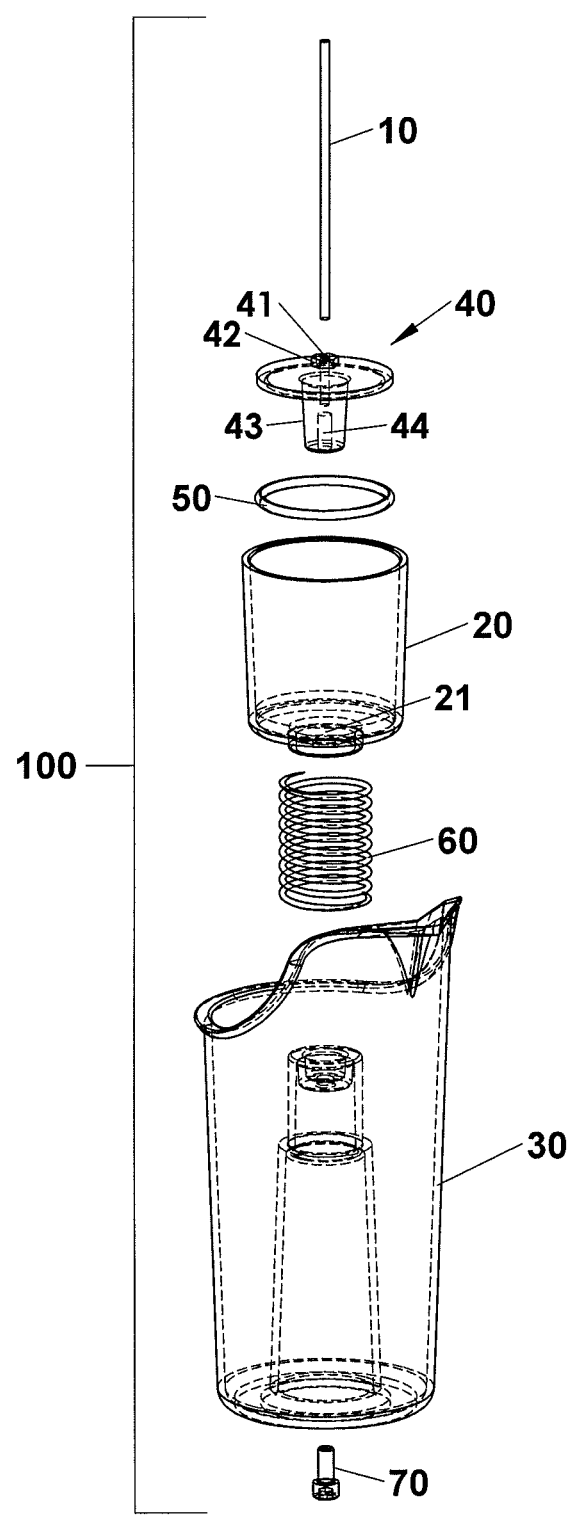
FIG. 7 is an exploded view of the multiple sump fuel sampler with catch can of FIG. 1.

Referring now to FIG. 7, the upper reservoir 20, which is comprised of a circular container with a bottom, which has a hole 21. In an embodiment, upper reservoir 20 is formed or molded from clear plastic, which facilitates visual inspection of the fuel it contains during use. The hole 21 allows fuel to drain from the upper reservoir 20 into the lower reservoir 30.

Now referring to FIG. 4 in more detail, upper reservoir 20 is made to hold fuel by means of end cap 40 and O-ring 50. End cap 40 is placed into the lower portion of the upper reservoir 20 with O-ring 50, such that pressure between the end cap 40 and the upper reservoir 20 will cause compression of the O-ring 50. Said compression results in a liquid tight seal being formed between end cap 40 and the inner bottom surface of the upper reservoir 20.

Referring again to FIG. 7, end cap 40 includes an upper hole 41 for receiving a rod 10. A lower hole 44 is for receiving screw 70 when the multiple sump fuel sampler with catch can 100 is assembled. End cap 40 is further comprised of an extended section 43, which is tapered as shown and whose size and taper angle match that of receiving socket 31 of lower reservoir 30, such that, when assembled, extended section 43 comes in contact with the inner wall of socket 31, as can be seen in FIG. 4. Referring to FIG. 7, end cap 40 has an extended hex portion 42, which facilitates tightening of screw 70 by providing a means to attach a wrench to counteract the torque on end cap 40 as screw 70 is tightened. In an embodiment of the invention, the end cap 40 is formed or fabricated from a clear material to improve visual inspection of fuel in the upper reservoir 20. End cap 40 has an outer diameter sized smaller than the inner diameter of the upper reservoir 20, thus gap 85 is present when upper reservoir 20 is positioned to drain into the lower reservoir 30, as shown in FIG. 6.

Figure 6:
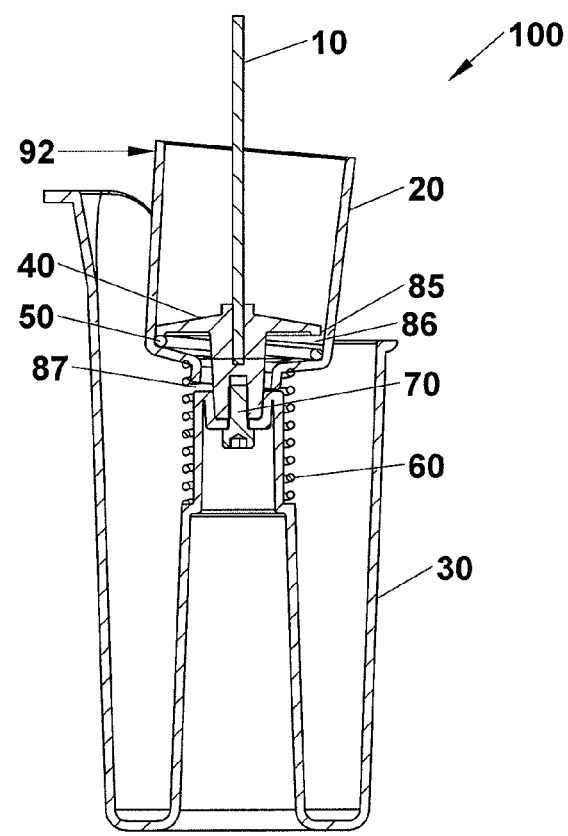
FIG. 6 is a cross-sectional view of the multiple sump fuel sampler with catch can of FIG. 1 with the self-closing valve in the open position.

Referring to FIG. 4 and FIG. 6, O-ring 50 is sized such that its outer diameter is larger than the inner diameter of upper reservoir 20 when in its natural state, i.e., not compressed. Thus, O-ring 50 must be slightly compressed when properly installed in the bottom inside of upper reservoir 20. This compression generates friction which holds O-ring 50 in the position shown in FIG. 4, even when the upper reservoir 20 is tilted for draining, as shown in FIG. 6. As described, O-ring 50 stays in the installed position regardless of what direction or angle upper reservoir 20 is positioned. O-ring 50 is comprised of an elastomer, which maybe clear or opaque.

Figure 2:
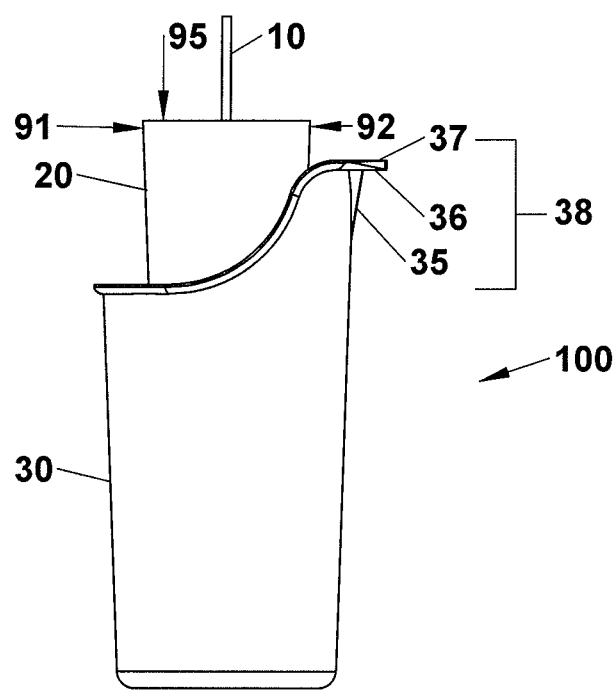
FIG. 2 is a side view of the multiple sump fuel sampler with catch can of FIG. 1.
Figure 5:
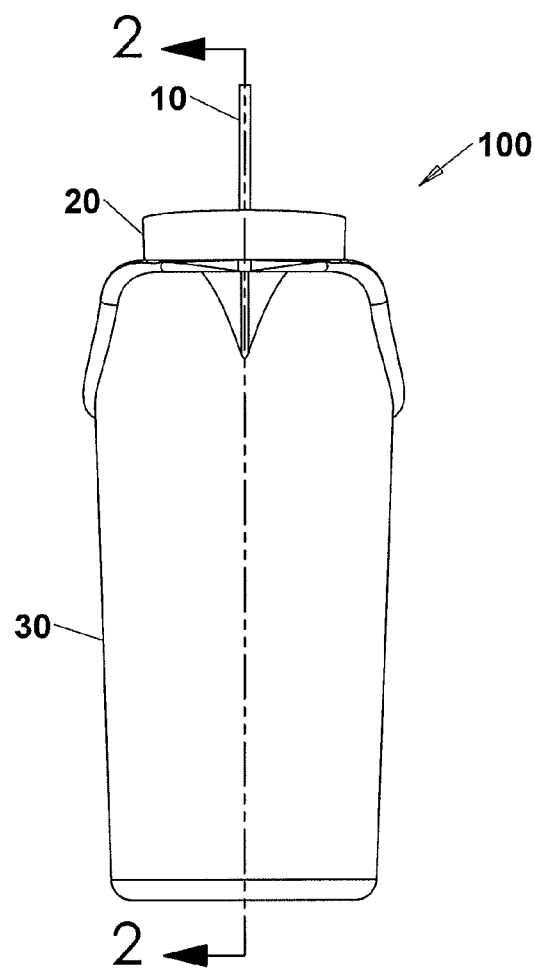
FIG. 5 is a front view of the multiple sump fuel sampler with catch can of FIG. 1 with the self-closing valve in the open position.

Referring to FIG. 7, rod 10 can be made of a metallic or non-metallic material of sufficient rigidity to maintain its straight shape even when under the axial force necessary to activate the aircrafts fuel sump valve (not shown). Rod 10 serves as a means to activate the fuel sump valve on an aircraft which requires upward force from a small rod. As shown in FIG. 1 and FIG. 2, rod 10 is sized such that it extends upward beyond upper reservoir 20 by a distance which allows for convenient activation of said fuel sump valve. In at least one embodiment, rod 10 has an outer diameter sized such that it is press fit into hole 41 of end cap 40. Rod 10 is therefore rigidly fixed to end cap 40 by this means of this attachment. Since end cap 40 is rigidly fixed to lower reservoir 30 by means of screw 70, rod 10 is therefore also rigidly fixed to lower reservoir 30. As such, movement or force applied to the lower reservoir 30 by a users hand is directly translated to rod 10, thus providing a means of activating an aircraft's fuel sump valve while the user holds lower reservoir 30.

Now referring to FIG. 4 and FIG. 7, lower reservoir 30 is described in further detail. In at least one embodiment, lower reservoir 30 is formed or fabricated from a clear or opaque metallic or non-metallic material. In this embodiment, the lower reservoir 30 is constructed of clear plastic to allow easy visual inspection of its contents and the level of liquid contained therein. Lower reservoir 30 includes an inner pedestal 33, which provides a receiving socket 31 for the extended portion 43 of end cap 40. The center of the receiving socket 31 contains a hole 32 through which screw 70 passes to engage in hole 44 of end cap 40. Inner pedestal 33 has a ledge 34 for providing support to the lower end of spring 60.

Now referring to FIG. 2, lower reservoir 30 is comprised of an upward extended section 38, which allows tipping of the lower reservoir 30 to a greater angle during emptying. Increasing the tip angle allows greater control over the aim and direction of fuel as it empties from lower reservoir 30 via pour spout 37. An increased tip angle during emptying also decreases the tendency of fuel to dribble down the outside of the lower reservoir 30 and, hence, decreases the likelihood that fuel will flow in a path not intended from pour spout 37. Pour spout 37 provides accuracy to the direction of the flow of fuel as lower reservoir 30 is tipped and emptied. An extended surface 36 projects beyond the outer surface 35 of pour spout 37. The distance of projection is selected to be greater than the distance that the fuel will naturally flow back up the surface of the material from which the lower reservoir 30 is constructed, based on the surface tension of the fuel, the force of gravity, and surface characteristics of the lower reservoir 30. By exceeding this distance with extended surface 36, fuel is kept from dribbling down the outside of lower reservoir 30 during tipping and emptying. As described above, extended section 38 and extended surface 36 combined with pour spout 37 are configured to keep fuel from being discharged in unwanted directions or locations during emptying of the lower reservoir 30.

Referring again to FIG. 4, spring 60 is described in further detail. Spring 60 can be constructed of metallic or non-metallic material such that a compression spring is formed. In at least one embodiment, the multiple sump fuel sampler with catch can 100 uses a spring 60 constructed of spring temper stainless steel wire. Spring 60 has an inner diameter and an outer diameter sized such that the lower end of spring 60 is contained on ledge 34. Spring 60 has a natural length selected such that the spring must be compressed to fit between the bottom surface of upper reservoir 20 and ledge 34. Thus, spring 60 applies an upward force on upper reservoir 20 when the multiple sump fuel sampler with catch can 100 is fully assembled. This upward force presses the upper reservoir 20 against o-ring 50 and end cap 40, which is rigidly fixed to lower reservoir 30. As a result, the upper reservoir 20 is held upright and a seal is formed between the end cap 40 and the lower inside of upper reservoir 20, which thusly is able to hold fuel.

As shown in FIG. 6, a lateral force in the direction of arrow 92 can be applied to the upper outside edge of the upper reservoir 20. When this force is of sufficient strength to overcome the resultant force generated by spring 60, upper reservoir 20 will tip as shown in FIG. 6. The level of force applied by spring 60 is selected such that O-ring 50 forms a full seal, but not with too high a force so that the amount of pressure required by one of the user's fingers in direction 92 would be uncomfortable or insufficient to tip the upper reservoir 20, as shown in FIG. 6.

With upper reservoir 20 tipped as shown in FIG. 6, gaps 85, 86, and 87 are created, which allow fuel in the upper reservoir 20 to drain through gap 85 to gap 86 to gap 87 in sequence and, finally, into the lower reservoir 30. By this means, tipping of the upper reservoir 20 in any direction around the central axis represented by rod 10 will similarly open gaps 85, 86, and 87, allowing fuel to drain from upper reservoir 20 into lower reservoir 30. Gaps 85 and 86 will be on the opposite side of upper reservoir 20 relative to the applied force, while gap 87 will be on the same side as the applied force. Examples of other such forces which may similarly tip the upper reservoir 20, like the force in direction 92, can be seen in FIG. 2 and FIG. 3 represented by arrows 91, 93, 94, and 95.

In operation, according to an embodiment of the invention, the multiple sump fuel sampler with catch can 100 is held in the user's hand. The user presses rod 10 upward against the airplane's fuel sump valve (not shown), which causes fuel to flow down from the fuel sump valve into upper reservoir 20. Rod 10 is fixed with reference to lower reservoir 30 and, therefore, allows control of the position and force applied to rod 10 through the user's hand, which may only grasp the lower reservoir 30 while operating the airplane's fuel sump valve. Once the user is satisfied with the quantity of fuel in the upper reservoir 20, he user then stops fuel flow into the upper reservoir 20 by releasing upward pressure on the airplane's fuel sump valve through rod 10. The user then visually inspects the fuel sample in upper reservoir 20 through its clear sides to determine if contamination of water or other foreign material is present in the sample.

Once visual inspection is complete, the fuel sample is transferred into the lower reservoir 30 by opening the self-closing valve located between the upper reservoir 20 and the lower reservoir 30. This self-closing valve is opened as shown in FIG. 6 when the user presses sideways on the upper portion of the upper reservoir 20 from any direction, as indicated by the arrows 91, 92, 93, 94 (in FIGS. 2 and 3) showing the direction of the applied force, or even by a slight downward force applied to an outer rim of the upper reservoir, as shown by arrow 95 (in FIG. 2). Once the fuel sample has drained from the upper reservoir 20 into the lower reservoir 30, the user releases side pressure and the self-closing valve closes. This process continues until all the fuel sumps on the aircraft have been checked, or until the lower reservoir 30 becomes full. When one of the above conditions occurs, the user empties the lower reservoir 30 by tipping it sideways such that the fuel pours out of lower reservoir 30 through pour spout 37 into the airplane's fuel tank or other container for proper disposal of sampled fuel.

In view of the above, embodiments of the present invention include a multiple sump fuel sampler with catch can 100 with both an upper and lower reservoir 20, 30 separated by a self-closing valve, which allows fuel to drain from the upper reservoir 20 into the lower reservoir 30 by gravity. Further, embodiments of the invention feature a lower reservoir 30 sized larger than the upper reservoir 20 such that a number of full volumes of the upper reservoir 20 can drain into the lower reservoir 30 without causing it to overflow. In at least one embodiment, the self-closing valve between the upper and lower reservoirs 20, 30 being an integral part of the bottom of the upper reservoir 20. Embodiments also feature both upper and lower reservoirs 20, 30 constructed of a clear material to allow easy inspection of fuel in both the upper and lower reservoirs 20, 30. Another feature of embodiments of the invention is that the multiple sump fuel sampler with catch can 100 can be operated through all functions with only one hand. Further, embodiments include a special pour spout 37 extension that keeps fuel from running back down the outside of the lower reservoir 30 during emptying. This allows dumping of the lower reservoir 30 without dribbling fuel in unwanted directions or areas. Another feature of embodiments of the invention is that both upper and lower reservoirs 20, 30 are open to the atmosphere at the top to allow fuel vapors to escape.

All references, including publications, patent applications, and patents cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) is to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A multiple sump fuel sampler with catch can adapted to be used on aircraft fuel sumps, comprising:
   an upper reservoir configured to hold a liquid;
   a lower reservoir coupled to the upper reservoir, the lower reservoir being larger than the upper reservoir;
   a self-closing valve attached at the juncture of the upper and lower reservoirs, the self-closing valve configured to, when open, allow liquid in the upper reservoir to drain into the lower reservoir; and
   a rod attached to the multiple sump fuel sampler with catch can, the rod configured to activate a fuel sump valve.

2. The multiple sump fuel sampler with catch can of claim 1, wherein the upper reservoir has an opening in a bottom portion through which a liquid can flow into the lower reservoir.

3. The multiple sump fuel sampler with catch can of claim 1, wherein the self-closing valve comprises an end cap, an O-ring, and a spring.

4. The multiple sump fuel sampler with catch can of claim 3, wherein the end cap is made from clear plastic.

5. The multiple sump fuel sampler with catch can of claim 3, wherein a diameter of the O-ring is larger than an inner diameter of the upper reservoir such that the O-ring must be compressed when installed in the bottom of the upper reservoir, and wherein the O-ring is configured to be held in place by friction with the upper reservoir.

6. The multiple sump fuel sampler with catch can of claim 3, wherein the end cap and O-ring are seated at the bottom of the interior of the upper reservoir, wherein the spring causes the end cap and O-ring to create a liquid-tight seal against the bottom of the interior of the upper reservoir.

7. The multiple sump fuel sampler with catch can of claim 6, wherein the liquid-tight seal can be broken by applying a lateral force against an upper portion of the upper reservoir, wherein breaking the liquid-tight seal allows a liquid in the upper reservoir to drain into the lower reservoir.

8. The multiple sump fuel sampler with catch can of claim 7, wherein the lateral force can be applied at any point around the circumference of the upper reservoir.

9. The multiple sump fuel sampler with catch can of claim 8, wherein the self-closing valve is configured such that the force needed to break the liquid-tight seal can be applied by one finger of a user.

10. The multiple sump fuel sampler with catch can of claim 6, wherein the liquid-tight seal can be broken by pushing downward on an outer rim of the upper reservoir, wherein breaking the liquid-tight seal allows a liquid in the upper reservoir to drain into the lower reservoir.

11. The multiple sump fuel sampler with catch can of claim 3, wherein the rod extends through at least a portion of the self-closing valve, through the interior of the upper reservoir and beyond an opening at the top of the upper reservoir.

12. The multiple sump fuel sampler with catch can of claim 11, wherein the rod is attached to the end cap and the end cap is attached to the lower reservoir, such that the rod is held in fixed relation to the lower reservoir.

13. The multiple sump fuel sampler with catch can of claim 12, wherein the rod is attached to the end cap via a press fit into an opening in the end cap.

14. The multiple sump fuel sampler with catch can of claim 12, wherein the end cap has an opening to receive a screw, and is attached to the lower reservoir via the screw which passes through an opening in the lower reservoir and fastens into the opening in the end cap.

15. The multiple sump fuel sampler with catch can of claim 3, wherein a bottom end of the spring is supported by a portion of the lower reservoir, and a top end of the spring abuts a bottom portion of the upper reservoir.

16. The multiple sump fuel sampler with catch can of claim 15, wherein the spring has a natural length selected such that the spring must be compressed to fit between the upper reservoir and lower reservoir.

17. The multiple sump fuel sampler with catch can of claim 1, wherein the upper reservoir is made from clear plastic.

18. The multiple sump fuel sampler with catch can of claim 1, wherein the lower reservoir is made from clear plastic.

19. The multiple sump fuel sampler with catch can of claim 1, wherein lower reservoir is sized and configured such that a user holding the multiple sump fuel sampler with catch can by the lower reservoir can operate the multiple sump fuel sampler with catch can with one hand only.

20. The multiple sump fuel sampler with catch can of claim 1, further comprising a pour spout located at a top edge of the lower reservoir.

21. The multiple sump fuel sampler with catch can of claim 20, wherein the pour spout includes an extended surface that projects laterally from the top edge of the reservoir that functions to preclude fuel from running down the outside of the lower reservoir during emptying.

\* \* \* \* \*